United States Patent [19]

Rossman et al.

[11] Patent Number: 5,116,977

[45] Date of Patent: * May 26, 1992

[54] HALOMETHYL-1,3,5-TRIAZINES CONTAINING AN AMINE-CONTAINING MOIETY

[75] Inventors: Mitchel A. Rossman, Minneapolis; James A. Bonham, Grant Township, Washington County, both of Minn.

[73] Assignee: Minnesota Mining and Manufacturing Company, St. Paul, Minn.

[*] Notice: The portion of the term of this patent subsequent to Jan. 15, 2008 has been disclaimed.

[21] Appl. No.: 640,706

[22] Filed: Jan. 14, 1991

Related U.S. Application Data

[63] Continuation of Ser. No. 241,383, Sep. 7, 1988, Pat. No. 4,985,562.

[51] Int. Cl.$^5$ .................................. C07D 413/12
[52] U.S. Cl. ........................ 544/113; 544/194; 544/204; 544/208; 544/209; 544/211; 544/212; 544/216; 544/219; 430/270
[58] Field of Search ............... 544/113, 194, 204, 208, 544/209, 211, 212, 216, 219

[56] References Cited

U.S. PATENT DOCUMENTS

| | | | |
|---|---|---|---|
| 3,488,269 | 1/1970 | Allen et al. | 204/159.23 |
| 3,495,987 | 2/1970 | Moore | 96/115 |
| 3,573,922 | 4/1971 | Rust | 96/115 |
| 3,617,288 | 11/1971 | Hartman | 96/90 |
| 3,640,718 | 2/1972 | Smith | 96/89 |
| 3,650,927 | 3/1972 | Chatham | 204/159.24 |
| 3,682,641 | 8/1972 | Casler et al. | 96/35.1 |
| 3,729,404 | 4/1973 | Morgan | 204/159.15 |
| 3,779,778 | 12/1973 | Smith et al. | 96/115 R |
| 3,905,815 | 11/1975 | Bonham | 96/68 |
| 3,933,682 | 1/1976 | Bean | 252/431 R |
| 3,954,475 | 5/1976 | Bonham et al. | 96/67 |
| 3,966,573 | 6/1976 | Bean | 204/159.23 |
| 3,987,037 | 10/1976 | Bonham et al. | 260/240 D |
| 4,181,323 | 2/1980 | Buhr | 430/281 |
| 4,239,850 | 12/1980 | Kita et al. | 430/281 |
| 4,259,432 | 3/1981 | Kondoh et al. | 430/281 |
| 4,366,228 | 12/1982 | Specht et al. | 430/281 |
| 4,391,687 | 7/1983 | Vesley | 204/159.16 |
| 4,476,215 | 10/1984 | Kausch | 430/281 |
| 4,505,793 | 3/1985 | Tamoto et al. | 204/159.16 |
| 4,758,497 | 7/1988 | Shah et al. | 430/193 |
| 4,933,452 | 6/1990 | White et al. | 544/113 |

FOREIGN PATENT DOCUMENTS

| | | |
|---|---|---|
| 0109291 | 6/1984 | European Pat. Off. . |
| 0305115A2 | 3/1989 | European Pat. Off. . |
| 2851641 | 5/1979 | Fed. Rep. of Germany . |
| 3517440 | 9/1985 | Fed. Rep. of Germany . |
| 3726001A1 | 2/1988 | Fed. Rep. of Germany . |
| 8560104 | 6/1980 | Japan . |

OTHER PUBLICATIONS

Kosar, Light Sensitive Systems, J. Wiley and Sons (New York 1965), pp. 361-369.
Ledwith, J. Oil Col. Chem. Assoc., 1976, 59, 167.
U. Von Gizycki, Angew. Chem. Int. Ed. Eng., 1971, 10, 403.
Wakabayashi et al., Bulletin of the Chemical Society of Japan, 1969, 42, 2924.

Primary Examiner—Johann Richter
Attorney, Agent, or Firm—Gary L. Griswold; Walter N. Kirn; David L. Weinstein

[57] ABSTRACT

Radiation-sensitive organo-halogen compounds having a photo-labile halomethyl-1,3,5-triazine moiety and at least one amine-containing moiety within one molecule. The compounds serve the dual purpose of photoinitiation and polymerization acceleration, thereby eliminating the need for the use of two separate compounds. The compounds of this invention are good photoinitiators, and compositions containing them are useful in printing, duplicating, copying, and other imaging systems.

14 Claims, No Drawings

HALOMETHYL-1,3,5-TRIAZINES CONTAINING AN AMINE-CONTAINING MOIETY

This is a continuation of application Ser. No. 241,383, filed Sept. 7, 1988, now U.S. Pat. No. 4,985,562.

BACKGROUND OF INVENTION

1. Field of the Invention

The present invention relates to photosensitive compounds that generate free radicals upon exposure to light. More particularly, it relates to derivatives of halomethyl-1,3,5-triazines.

2. Discussion of the Prior Art

Compounds that decompose to generate free radicals (free radical generating agents) upon exposure to light are well known in the graphic arts. Organic halogen compounds, which are capable of generating free radicals such as a chlorine free radical or a bromine free radical upon exposure to light, have been widely used as photoinitiators in photopolymerizable compositions, as photoactivators in free radical photographic compositions, and as photoinitiators for reactions catalyzed by acids formed by light. The spectral sensitivity of these compositions may be broadened by the addition of sensitizers which in essence transfer their absorbed energy to the organic halogen compound. The use of such halogen compounds in photopolymerization processes and free radical photographic processes have been described in Kosar, *Light-Sensitive Systems*, J. Wiley & Sons (New York, 1965), pp. 180-181, 361-370

Halomethyl-1,3,5-triazines are known to be initiators for a number of photochemical reactions. They can be employed to produce free radicals by actinic radiation for initiating polymerization or color changes and for initiating secondary reactions upon liberation of acid by the interaction of the free-radicals when hydrogen donors are present.

Examples of the use of the halomethyl-1,3,5triazines in the free radical polymerization of acrylate monomers are described in U.S. Pat. No. 3,905,815; U.S. Pat. No. 3,617,288; U.S. Pat. No. 4,181,752; U.S. Pat. No. 4,391,687; U.S. Pat. No. 4,476,215; and DE 3,517,440. U.S. Pat. No. 3,779,778 discloses the photoinitiated acid catalyzed decomposition of pyranyl ether derivatives to produce photosolubilizable compositions useful as positive printing plates. Chromophore substituted styryl-1,3,5-triazines and their uses are disclosed in U.S. Pat. No. 3,987,037 and U.S. Pat. No. 3,954,475. Radiation sensitive compositions containing bi- and polyaromatic substituted triazines are disclosed in U.S. Pat. No. 4,189,323.

Co-initiators usually comprise two compounds, a light-sensitive compound usually identified as a photoinitiator, and an activator or additive compound which in the presence of the photoinitiator is not significantly directly excited by the activating radiation, but instead forms a free radical in response to the exposure of the photoinitiator. Known classes of such additives include amines, sulfinic acids and sulfinic acid esters, sulfones, alpha- and beta-dicarbonyl compounds, such as bornanedione and acetylacetone, phosphines, phosphites, and stannates.

An effective system which consists of an amine and an aromatic carbonyl compound is Michler's ketone and benzophenone as described in U.S. Pat. No. 3,682,641. A number of aromatic carbonyl compounds have been disclosed as being useful with amine additives to form co-initiators of many kinds. Such mixtures are described by Ledwith, J. Oil Col. Chem. Assoc. 1976, 59, 167. These compounds include phenones, including cyclic ketones such as benzophenone, fluorenones, anthraquinones, and anthranones More recently, 3-keto-coumarins have been shown to be effective with Michler's ketone, as described in U.S. Pat. No. 4,366,228 and have been highly effective in photopolymerization compositions of various kinds Other examples of similar systems are described in U.S. Pat. Nos. 3,488,269; 3,966,573; 3,933,682; 3,729,404; 3,573,922; and 3,650,927.

SUMMARY OF THE INVENTION

This invention provides radiation-sensitive organohalogen compounds having good sensitivity in the visible and ultraviolet range of the spectrum, thus rendering them suitable for use in radiation-sensitive compositions. This invention provides compounds that have a photo-labile halomethyl-1,3,5-triazine moiety and an amine-containing moiety within one molecule, thereby eliminating the need for the use of two separate compounds. The compounds of this invention are good photoinitiators, and photopolymerizable and photocrosslinkable compositions containing them are useful in printing, duplicating, copying, and other imaging systems.

This invention provides 1,3,5-triazine compounds having at least one halomethyl substituent on a carbon atom of the triazine nucleus and an amine-containing moiety attached to another carbon atom of the triazine nucleus, said amine-containing moiety containing at least one tertiary amine group having at least one alkyl substituent, said alkyl substituent having a hydrogen atom on the carbon atom adjacent to the nitrogen atom of the amine. This carbon atom is referred to as the α-carbon atom. The nitrogen atom of the amine cannot be attached directly to the 1,3,5-triazine nucleus by a covalent bond or by a conjugated linkage. The compounds of this invention are capable of accelerating the rate of polymerization, with or without the presence of a sensitizing dye, upon stimulation by actinic radiation at a wavelength of about 250 to 900 nanometers.

The compounds of this invention are useful as photoinitiators for photosensitive compositions and elements. They can be incorporated in photopolymerizable compositions and printing compositions useful for producing printing plates such as lithographic plates, relief plates or gravure plates, photoresists and photographic elements, and photosensitive resist-forming compositions with which visible images are obtained upon exposure to light.

DETAILED DESCRIPTION OF THE INVENTION

Halomethyl-substituted 1,3,5-triazine compounds of this invention can be represented by the general formula wherein

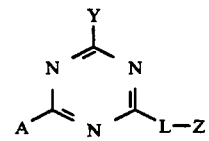

A represents a member selected from the group consisting of mono-, di- and trihalomethyl groups, Y represents a member selected from the group consisting of A, L-Z, NH₂, NHR, NR₂, OR, and R' where R independently represents a substituted or unsubstituted alkyl group, preferably having 1 to 6 carbon atoms, or a substituted or unsubstituted aryl group, and R' represents a substituted or unsubstituted alkyl group, preferably having 1 to 6 carbon atoms, a substituted or unsubstituted aryl group, a substituted or unsubstituted alkenyl group, preferably having 2 to 6 carbon atoms, or a substituted or unsubstituted heterocyclic aromatic group, Z represents an amine-containing moiety containing at least one tertiary amine group having at least one alkyl substituent on the amine nitrogen atom, said at least one alkyl substituent having a hydrogen atom on the carbon atom adjacent to the amine nitrogen atom, provided that the amine nitrogen atom is not directly attached to the 1,3,5-triazine nucleus by a covalent bond or by a conjugated linkage, e.g., via an aryl group or a vinyl group, and L represents a group linking the amine-containing moiety to the triazine nucleus.

Halomethyl groups that are suitable for the present invention include chloro-, bromo-, and iodomethyl groups, with chloro- and bromomethyl groups being preferred. Trihalomethyl groups are preferred; most preferred are trichloromethyl and tribromomethyl groups.

Y represents any of a variety of substituents that are useful in modifying the physical, e.g., solubility, or chemical properties of the molecule, and preferably represents A, L—Z, or R'. When Y represents A, the maximum number of halomethyl groups per triazine nucleus can be made available for free radical generation. When Y represents L—Z, the chemical composition for both L—Z groups can be the same, or it can be different, depending on the composition of linking group L, amine-containing group Z, or both. When Y represents R', and in particular when R' represents an aryl, aralkenyl, or heteroaromatic group, the spectral sensitivity of the molecule can be varied, based on the photochemical response of R' to actinic radiation.

When R or R' represents an aryl group, it is preferred that the group have a maximum of five rings, more preferably three rings, and most preferably one ring.

When R or R' represents a substituted group, the particular identity of the substituents is not critical. However, the substituents should not adversely affect the photoinitiation characteristics of the compounds of this invention.

Z can be selected from tertiary amine groups substituted with at least one alkyl group having a hydrogen atom on the α-carbon atom, and is most preferably selected from tertiary amine groups substituted with three alkyl groups, such that there are a total of eight hydrogen atoms on the three α-carbon atoms. There is no upper limit on the number of amine-containing moieties per triazine nucleus; there is no upper limit on the number of triazine nuclei per amine-containing moiety; however, there must be at least one amine-containing moiety per triazine nucleus. Preferably, the number of amine-containing moieties per triazine nucleus ranges from 1 to 2 to 2 to 1. If more than one amine-containing moiety is present per triazine nucleus, they can be from different species from the same generic class.

Amine containing moieties designated by Z can be selected from tertiary amine groups represented by the following general formula II:

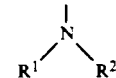

wherein

R¹ represents a substituted or unsubstituted alkyl group, preferably having 1 to 10 carbon atoms, or a substituted or unsubstituted aryl group, preferably having 1 to 2 rings, R² represents a substituted or unsubstituted alkyl group, preferably having 1 to 10 carbon atoms, or a substituted or unsubstituted aryl group, preferably having 1 to 2 rings, or R¹, R², and N can form a heterocyclic aliphatic or aromatic ring, preferably having no more than six ring members, provided that R¹ has at least one hydrogen atom on the α-carbon atom.

L represents a group that links the amine-containing moiety or moieties to the triazine nucleus. The precise identity of L is not critical, but it should be selected so that it does not interfere with or adversely affect the light sensitivity of the compound. Furthermore, L should be chosen so that it does not connect the chromophore of the halomethyl-1,3,5-triazine nucleus and the amine nitrogen atom either directly by a covalent bond or by a conjugated linkage. L can be a single group or can be formed from a combination of groups. Groups that are suitable for linking groups include carbamato (—NHCO₂—), urea (—NHCONH—), amino (—NH—), amido (—CONH—), aliphatic, e.g., having up to 10 carbon atoms, alkyl, e.g., having up to 10 carbon atoms, alkenyl, e.g., having up to 10 carbon atoms, aryl, e.g., having one ring, ester (—CO₂—), ether (—O—), and combinations thereof. Based on ease of synthesis, the most preferred groups attached directly to the triazine nucleus are carbamato, urea, amino, alkenyl, aryl, and ether. Whenever the group directly attached to the triazine nucleus is either alkenyl group or aryl group, another group must be interposed between the alkenyl group or aryl group and the amine nitrogen atom to prevent the amine-containing group from forming a conjugated bond with the triazine nucleus.

The following exemplify typical —L—Z group combinations:

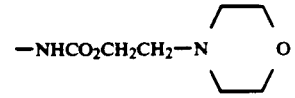

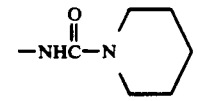

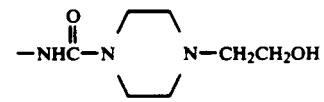

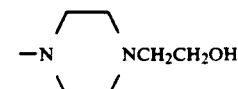

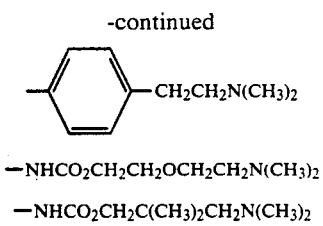

—NHCO₂CH₂CH₂OCH₂CH₂N(CH₃)₂

—NHCO₂CH₂C(CH₃)₂CH₂N(CH₃)₂

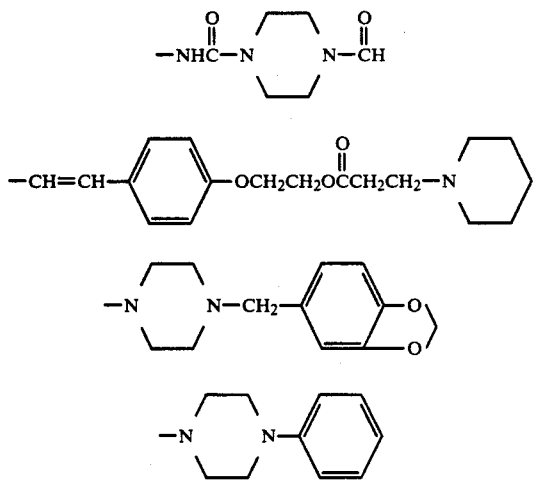

One method of preparing the compounds of this invention is by the addition reaction of isocyanato-substituted halomethyl-1,3,5-triazines with amines having groups reactive with the isocyanate group. The isocyanato substituted triazines may be prepared from the corresponding amino derivative according to the procedure of U. Von Gizycki, Angew. Chem. Int. Ed. Eng., 1971, 10, 403. Isocyanato-1,3,5-triazines suitable for this reaction include:

2,4-bis(trichloromethyl)-6-isocyanato-1,3,5-triazine
2-isocyanato-4-methyl-6-trichloromethyl-1,3,5-triazine
2-isocyanato-4-phenyl-6-trichloromethyl-1,3,5-triazine
2-isocyanato-4-methoxy-6-trichloromethyl-1,3,5-triazine
2-isocyanato-4-(p-methoxyphenyl)-6-trichloromethyl 1,3,5-triazine
2-isocyanato-4 (p-methoxystyryl)-6-trichloromethyl 1,3,5 triazine
2-isocyanato-4-(m,p-dimethoxyphenyl)-6 trichloromethyl 1, 3,5-triazine Typical amines capable of combining with the isocyanato group include N,N-dimethylethanolamine, 4-(dimethylamino)phenethyl alcohol, 2-{[2-(dimethylamino)ethyl]methylamino}ethanol, 3-dimethylaminopropylamine, and piperidine.

The isocyanate addition reaction can be carried out in the presence of solvents including toluene, pyridine, benzene, xylene, dioxane, tetrahydrofuran, etc., and mixtures of solvents. The duration and temperature of the reaction is dependent on the particular compounds and the catalyst employed. Generally, temperatures ranging from about 25° C. to 150° C. for from about one to seventy-two hours are sufficient for the reaction. Preferably, the reaction is carried out at room temperature from three to seventy-two hours. The preferred catalyst is di-n-butyltin dilaurate.

Other methods for preparing the compounds of this invention include the cotrimerization of organic nitriles having an amine-containing substituent with haloacetonitriles in accordance with the teachings of Wakabayashi et al, Bulletin of the Chemical Society of Japan, 1969, 42, 2924–30; the condensation reaction of an aldehyde compound having an amine-containing substituent in accordance with the teachings of U.S. Pat. No. 3,987,037; the nucleophilic displacement reactions on halomethyl-1,3,5-triazines using amine-containing compounds having free hydroxy or amino groups.

The sensitivity of polymerizable compositions containing the compounds of this invention to actinic radiation of a particular wavelength range can be increased by the incorporation of known ultraviolet and visible light sensitizers including cyanine, carbocyanine, merocyanine, styryl, acridine, polycyclic aromatic hydrocarbons, polyarylamines, and amine-substituted chalcones. Suitable cyanine dyes are described in U.S. Pat. No. 3,495,987. Suitable styryl dyes and polyarylamines are described in Kosar, Light Sensitive Systems, J. Wiley and Sons (New York, 1965), pp. 361–369. Polycyclic aromatic hydrocarbons that are useful as sensitizers, e.g., 2-ethyl-9,10-dimethoxyanthracene, are disclosed in U.S. Pat. No. 3,640,718. Amino substituted chalcones that are useful as sensitizers are described in U.S. Pat. No. 3,617,288.

The compounds of this invention can be used in photosensitive compositions in combination with other photoinitiators including benzophenones, benzoin ethers, thioxanthone, benzil and Michler's ketone. The compounds of this invention can be substituted for the triazines used in conjunction with dialkylamimo aromatic carbonyl compounds disclosed in U.S. Pat. No. 4,259,432; with 2-(benzoylmethylene)-5-benzothiazolidene thiazole -4-1 compounds disclosed in E application 0109291, May 23, 1984; with 3-keto-substituted coumarin compounds disclosed in U.S. Pat. No. 4,505,793; and with those compounds described in U.S. Pat. No. 4,239,850; Jpn. Kokai Tokkyo Koho JP 60 60,104 (85 60104); and Ger. Offen 2,851,641.

Photopolymerizable compositions in which the compounds of this invention can be used advantageously typically comprise an unsaturated, free radical initiated, chain propagating addition polymerizable compound, a compound of this invention, and, optionally, one or more fillers, binders, dyes, polymerization inhibitors, color precursors, oxygen scavengers, etc. The compounds of this invention should be present in an amount sufficient to initiate polymerization of said polymerizable compound. For every 100 parts of polymerizable compound there can be present from 0.005 to 10 parts of the compound of this invention, from 0 to 200 parts of filler, from 0 to 200 parts of binder, and from 0 to 10 or more parts of dyes, polymerization inhibitors, color precursors, oxygen scavengers, etc, as may be needed for a particular use of the photopolymerizable compositions. Preferably, for each 100 parts of polymerizable compounds, 1 to 7.5 parts of the compound of this invention and from 25 to 150 parts of binder are used.

Unsaturated, free-radical initiated, chain-propagating addition polymerizable compounds suitable for the compositions of this invention include alkylene or polyalkylene glycol diacrylates, e.g., ethylene glycol diacrylate, diethylene glycol diacrylate, glycerol diacrylate, glycerol triacrylate, ethylene glycol dimethacrylate, 1,3-propanediol dimethacrylate, 1,2,4-butanetriol timmethacrylate, 1,4-cyclohexanediol diacrylate, pentaerythritol tetramethacrylate, pentaerythritol triacrylate, sorbitol hexacrylate; bis[1-(3-acryloxy-2-hydroxy)]-p-propoxyphenyl dimethylmethane, bis[1-(2-acryloxy)]-p- ethoxyphenyldimethylmethane, tris hydroxyethylisocyanurate trimethacrylate, the bis-acrylate and the bis-methacrylates of polyethylene glycols of molecular weight 200–500 and the like; unsaturated amides, e.g., methylene bis-acrylamide, methylene bis-methacrylamide, 1,6-hexamethylene bis-acrylamide, diethylene triamine trisacrylamide, beta-methacrylaminoethyl methacrylate; vinyl esters such as divinyl succinate, divinyl adipate, divinyl phthalate. The preferred unsaturated compounds include pentaerythritol tetracrylate, bis[p-(3-acryloxy-2-hydroxypropoxy)phenyl] dimethylmethane, and bis[p-(2-acryloxyethoxy)phenyl] dimethylmethane. Mixtures of these esters can also be used as can mixtures of these esters with alkyl esters of acrylic acid and methacrylic acid, including such esters as methyl acrylate, methyl methacrylate, ethyl acrylate, isopropyl methacrylate, n-hexyl acrylate, stearyl acrylate, allyl acrylate, diallyl phthalate, and the like.

To prepare photosensitive compositions of this invention, the components can be admixed in any order and stirred or milled to form a solution or uniform dispersion. Photosensitive elements can be made by coating a photosensitive composition on a suitable base or support and drying the coating. The dry thickness typically ranges from about 0.00005 to about 0.075 inch.

Suitable bases or supports for the photosensitive compositions include metals, e.g., steel and aluminum plates, sheets and foils, and films or plates composed of various film-forming synthetic or high polymers, including addition polymers, e.g. vinylidene chloride, vinyl chloride, vinyl acetate, styrene, isobutylene polymers and copolymers; linear condensation polymers e.g., polyethylene terephthalate, polyhexamethylene adipate, polyhexamethylene adipamide/adipate.

The invention will be more specifically illustrated by the following examples. The value of λmax was measured in tetrahydrofuran, unless otherwise indicated.

EXAMPLE 1

To a solution containing 0.01 mol 4-(2-hydroxyethyl)morpholine and 12 drops di-n-butyltin dilaurate in 40 ml dry toluene was added a solution of 0.01 mol 2,4-bis(trichloromethyl)-6-isocyanato-1,3,5-triazine in toluene. The reaction mixture was stirred at room temperature under $N_2$ for 24–72 hrs. The solvent was removed under reduced pressure by means of a rotary evaporator and the residue was loaded upon a silica gel column (100 g packed with dichloromethane) and eluted with dichloromethane. The major compound was collected and the solvent was removed by means of a rotary evaporator to yield product. The product had a melting point of 210°–213° C. and a λmax of 234 nm. The structure of the product is shown below.

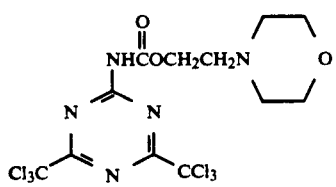

EXAMPLE 2

The procedure of Example 1 was repeated, with the only exception being that piperidine was used in place of -(2-hydroxyethyl)morpholine. The product had a melting point of 164°–167° C. and a λmax of 246 nm. The structure of the product is shown below.

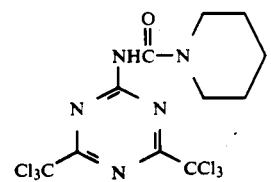

EXAMPLE 3

The procedure of Example 1 was repeated, with the only exception being that diisopropylamine was used in place of 4-(2-hydroxyethyl)morpholine. The product had a melting point of 190°–193° C. and a λmax of 250 nm. The structure of the product is shown below.

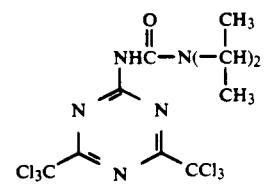

EXAMPLE 4

The procedure of Example 1 was repeated, with the only exception being that 1-(2-hydroxyethyl)piperazine was used in place of 4-(2-hydroxyethyl)morpholine. The product had a melting point of 120°–123° C. and a λmax of 243 nm. The structure of the product is shown below.

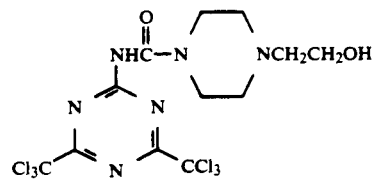

EXAMPLE 5

To a solution of 2.3 mmol 2,4,6-tris(trichloromethyl)-1,2,5-triazine in 25 ml toluene was added 1 equivalent of 1-(2-hydroxyethyl)-piperazine. The reaction mixture was stirred at room temperature for 24 hours under a nitrogen atmosphere. The solvent was removed by means of a rotary evaporator under reduced pressure, and the residue was dissolved in a small amount of dichloromethane, loaded upon a column of silica gel (100 g packed in hexane), and eluted with hexane. The appropriate fractions were pooled, and the solvent was removed by means of a rotary evaporator to yield product. The product was a gum. The structure of the product is shown below.

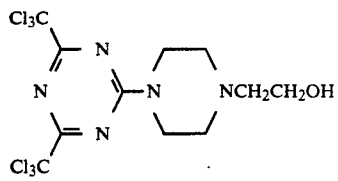

EXAMPLE 6

This example illustrates the preparation of photosensitive elements containing the halomethyl-1,3,5-triazines of this invention. The spectral response of the compounds in such elements is also shown.

A solution was prepared from 74.24 g azeotrope of 1-propanol and water (71.8% 1-propanol/28.2% water), 4.32 g pentaerythritol tetraacrylate ("Sartomer" monomer SR-295, Arco Chemical Company), 5.64 g oligomer (prepared according to U.S. Pat. No. 4,228,232 and 60.9% in methyl ethyl ketone), 0.30 triethylamine, and 14.88 g a 1:1 mixture of polyvinyl acetate-methylal resin ("Formvar" 12/85T, Union Carbide Corp.) and red pigment (Pigment Red 48, C.I. 15865) (9.4% by weight solution of the azeotrope). To 2.5 g of this solution was added 2.5 mg dimethylaminobenzylacetone (DMBA), 10 mg initiator, and the resulting solution was shaken in the dark for 15 minutes. The solution was filtered through glass wool and coated onto a grained, anodized aluminum plate with a #12 Mayer bar. The plate was dried at 66° C. for two minutes and cooled to room temperature. Over this coating was applied a topcoat formulation (prepared from 5.00 g carboxymethyl cellulose ether (CMC-7L), 0.26 g surfactant ("Triton" X-100) (10% in water), and 95.00 g water) with a #14 Mayer bar. The coating was carefully dried with a heat gun. The plates were exposed for five seconds in air on top of a draw-down glass in a 3M Seventy exposure unit equipped with a 2 kw photopolymer bulb through a π2, 21 step Stouffer step tablet. The plates were soaked in developer solution prepared from 784.40 g deionized water, 16.70 g sodium metasilicate pentahydrate, 33.40 g 1-propanol, and 0.50 g surfactant ("Dowfax-2Al", Dow Chemical Company) (45% solution in water) for 15 sec and rubbed 10 times with a 4"×4" cotton pad. The relative sensitivities for the triazines of Examples 1-5 are shown in Table 2.

TABLE 2

| Initiator | Solid Step |
|---|---|
| Example 1 | 12 |
| Example 2 | 13 |
| Example 3 | 13 |
| Example 4 | 11 |
| Example 5 | 8 |

Various modifications and alterations of this invention will become apparent to those skilled in the art without departing from the scope and spirit of this invention, and it should be understood that this invention is not to be unduly limited to the illustrated embodiments set forth herein.

What is claimed is:

1. A 1,3,5-triazine compound having at least one halomethyl substituent on a carbon atom of the triazine nucleus and at least one amine-containing moiety attached to another carbon atom of the triazine nucleus, said at least one amine-containing moiety containing at least one tertiary amine group having three alkyl substituents on the amine nitrogen atom, said alkyl substituents having a hydrogen atom on the carbon atom adjacent to the amine nitrogen atom, provided that the amine nitrogen atom is not directly attached to the 1,3,5-triazine nucleus by a covalent bond or by a conjugated linkage.

2. A compound of claim 1 wherein said at least one halomethyl group is a trihalomethyl group.

3. The compound o claim 2 wherein said trihalomethyl group is a member selected from the group consisting of trichloromethyl group, tribromomethyl group, and triiodomethyl group.

4. The compound of claim 1 wherein said amine-containing moiety comprises tertiary alkyl amines having 1 to 6 carbon atoms per alkyl group.

5. A compound having the formula:

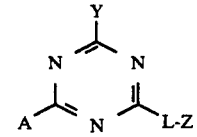

wherein
A represents a member selected from the group consisting of mono-, di- and trihalomethyl groups,
Y represents a member selected from the group consisting of A, L—Z, $NH_2$, NHR, $NR_2$, OR, and R'', where R independently represents a substituted or unsubstituted alkyl group, or a substituted or unsubstituted aryl group, R' represents a substituted or unsubstituted alkyl group, a substituted or unsubstituted aryl group, a substituted or unsubstituted alkenyl group, or a substituted or unsubstituted alkyl group heterocyclic aromatic group,
Z represents an amine-containing moiety selected from tertiary amine groups substituted with three alkyl groups, said alkyl groups having a hydrogen atom on the carbon atom adjacent to the amine nitrogen atom, provided that the amine nitrogen atom is not directly attached to the 1,3,5-triazine nucleus by a covalent bond or by a conjugated linkage, and
L represents a group linking the amine-containing moiety to the triazine nucleus.

6. The compound of claim 5 wherein A represents a trihalomethyl group.

7. The compound of claim 6 wherein the trihalomethyl group is a member selected from the group consisting of trichloromethyl, tribromomethyl, and triiodomethyl.

8. The compound of claim 7 wherein the trihalomethyl group is a member selected from the group consisting of trichloromethyl and tribromomethyl.

9. The compound of claim 5 wherein Y represents A.

10. The compound of claim 5 wherein Y represents L-Z.

11. The compound of claim 5 wherein R' represents a substituted or unsubstituted aryl group.

12. The compound of claim 5 wherein R' represents a substituted or unsubstituted heterocyclic aromatic group.

13. The compound of claim 5 wherein R' represents a substituted or unsubstituted alkenyl group.

14. The compound of claim 5 wherein said amine-containing moiety comprises tertiary alkyl amines having 1 to 6 carbon atoms per alkyl group.

* * * * *

UNITED STATES PATENT AND TRADEMARK OFFICE
CERTIFICATE OF CORRECTION

PATENT NO. : 5,116,977
DATED : May 26, 1992
INVENTOR(S) : Rossman et al.

It is certified that error appears in the above-indentified patent and that said Letters Patent is hereby corrected as shown below:

Title Page:

Item [75] Inventors "Mitchel" should be --Mitchell--.

Item [56] Referenes Cited , first line of U.S. PATENT DOCUMENTS, "4,181,323" should be --4,189,323--.

Col. 1, line 31, there should be a period after "370".

Col. 1, line 39, "1,3,5triazines" should be --1,3,5-triazines--.

Col. 2, line 5, "anthranones More" should be --anthranones. More--.

Col. 2, line 9, "kinds Other" should be --kinds. Other--.

Col. 7, line 68, "-(2-" should be --4-(2---.

Col. 9, line 39, "π2," should be --√2,--.

Col. 10, line 8, "o" should be --of--.

Col. 10, line 28, "R"" should be --R'--.

Signed and Sealed this

First Day of November, 1994

Attest:

BRUCE LEHMAN

Attesting Officer

Commissioner of Patents and Trademarks